United States Patent [19]

Fukuda

[11] Patent Number: 4,467,805

[45] Date of Patent: Aug. 28, 1984

[54] SKIN CLOSURE STAPLING DEVICE FOR SURGICAL PROCEDURES

[76] Inventor: Mamoru Fukuda, 1260 Hardy, Bridge City, Tex. 77611

[21] Appl. No.: 411,470

[22] Filed: Aug. 25, 1982

[51] Int. Cl.³ .............................................. A61B 17/08
[52] U.S. Cl. ............................ 128/334 C; 128/334 R; 128/335; 227/DIG. 1
[58] Field of Search ............ 128/334 R, 335, 336–337; 227/DIG. 1, DIG. 1 A–DIG. 1 C; 29/243.56, 766

[56] References Cited

U.S. PATENT DOCUMENTS

| | | | |
|---|---|---|---|
| 3,068,870 | 12/1962 | Levin | 227/DIG. 1 C |
| 3,357,296 | 12/1967 | Lefever | 227/DIG. 1 |
| 3,385,299 | 5/1968 | Le Roy | 227/DIG. 1 C |
| 3,516,409 | 6/1970 | Howell | 128/335 |
| 3,568,276 | 3/1971 | Morgan | 128/335 |
| 3,802,438 | 4/1974 | Woluek | 227/DIG. 1 C |
| 3,825,010 | 7/1974 | McDonald | 227/DIG. 1 C |
| 3,933,158 | 1/1976 | Haverstock | 128/335 |
| 4,114,624 | 9/1978 | Haverstock | 128/303 R |
| 4,259,959 | 4/1981 | Walker | 128/337 |

Primary Examiner—C. Fred Rosenbaum
Assistant Examiner—Gene B. Kartchner
Attorney, Agent, or Firm—Gunn, Lee & Jackson

[57] ABSTRACT

A skin opening and closure device for surgical procedures incorporates elongated flexible locking strips having elongated locking ridge means formed thereon which are adapted to be placed in interlocking assembly and capable of being separated and relocked, as desired. A plurality of half staples are provided, each of which is secured to respective ones of the locking strips to thereby define staple assemblies. Each of the staple assemblies incorporates skin penetrating elements and are adapted to be bent intermediate the extremities thereof to establish a secure skin retaining relation with the skin of the patient to provide a secure closure at the surgical incision. The staples, preferably, incorporate spaced pairs of skin penetrating projections which are originally positioned in substantially parallel relation, and which are adapted to be positioned in opposed, skin retaining relation upon bending of the staple. In use, the staples of the device are brought into engaging assembly with the skin of the patient at the site of the intended incision. Thereafter, the locking strips are separated in zipper-like manner to expose the skin for incision. After completion of the procedure, the locking strips are brought into interlocked relation by manual pressure or by zipper-like closure means to thereby close the incision.

19 Claims, 24 Drawing Figures

SKIN CLOSURE STAPLING DEVICE FOR SURGICAL PROCEDURES

FIELD OF THE INVENTION

This invention relates generally to surgical procedures wherein incisions are closed by means of stapling following completion of the surgery. More specifically, the present invention concerns utilization of staples having spaced pairs of skin penetrating elements to ensure that the skin at the incision is brought into non-overlapping, intimately engaging relation. Also, the invention concerns the provision of surgical stapling apparatus which is affixed to the patient prior to incision, may be selectively opened to permit surgical incision, and may be closed in zipper-like fashion to quickly and efficiently close the incision.

BACKGROUND OF THE INVENTION

Following surgical procedures and for purposes of tissue repair, body openings formed by the incision, tearing or cutting may be efficiently closed by securing the body tissue in intimate assembly. Such skin closing is typically accomplished by suturing, where a curved needle with a thread-like suture attached through an eyelet thereof may be passed through the skin and may be secured by means of a surgical knot. Typically, a number of sutures are required to accomplish efficient closure of a surgical incision.

Another method for accomplishing closure of a surgical incision or wound is to bring opposed skin portions into intimate assembly and then secure the same by means of staples. Typical staples are formed such as shown in FIGS. 6 and 7. Suitable stapling apparatus is typically utilized to deform the staples in assembly with the skin tissue of the patient, resulting in a finished staple configuration such as shown in FIG. 7.

One of the problems with application of staples to secure skin portions in assembly is the difficulty of maintaining opposed skin portions in abutting but non-overlapped relation. As shown in FIG. 7, opposed skin portions can easily become overlapped. The obvious result is improper healing and development of a surgical scar of undesirable configuration.

Through the use of sutures, the skin of the patient can be easily brought into proper abutting relation to ensure efficient healing. One of the problems with suturing, however, is that it is a time consuming procedure, thereby typically requiring the surgeon and patient to spend more time in the operating theatre than is desired for efficient utilization of the operatory. It is desirable, therefore, to provide a means for accomplishing efficient and quick closure of the patient to thereby minimize the time requirements for completion of the surgical procedure. It is also desirable to provide a system for accomplishing efficient closure of the patient and yet which also ensures that the skin of the patient be brought into intimate, non-overlapping relation through the use of stapling apparatus.

SUMMARY OF THE INVENTION

In accordance with the present invention, surgical staples are provided having an elongated staple bar capable of being bent intermediate the extremities thereof. The staple also incorporates a plurality of skin penetrating elements which extend transversely from the elongated staple bar and which are arranged in pairs at each extremity of the staple bar. The staple bar is capable of being bent between the centermost skin penetrating elements, causing the skin penetrating elements to be oriented in spaced, opposed relation when the staple is finished and properly installed to close the incision of the patient. The opposed pairs of skin penetrating elements maintain the skin and adjacent body tissue of the patient in intimate, non-overlapping relation to thus provide for efficient heating of the skin and body tissue and ensuring against development of an undesirably shaped scar at the incision.

For efficient closure of the surgical incision, the present invention incorporates a pair of elongated flexible locking strips, each of which incorporates elongated locking projections and grooves which interfit in interlocking relation so as to define a separatable closure. Each of the locking strips may be composed of a flexible plastic material such as polyethylene, for example. The locking strips may be brought into assembly or separated by manual application of force, if desired. Each of the elongated locking strips may have an opening tab attached thereto for the purpose of facilitating manual selective separation thereof for as much of the locking strips which is necessary to expose the skin of the patient for surgery.

A plurality of half staples are secured in spaced relation along each of the locking strips. The half staples correspond when the locking strips are in assembly to define staple assemblies which are engaged into the skin and body tissues of the patient to establish structural interconnection with the skin and body tissues before the surgical incision is made. Following the surgical procedure, the locking strips are brought into interlocking assembly to thereby force the skin of the patient into intimate proper related assembly at the incision. The locking strips are pliable thus permitting bending to conform the staple assembly for an incision of any desired configuration.

Through utilization of the skin opening and closure apparatus of the present invention, surgical procedures are conducted as follows: An elongated staple assembly is provided having a pair of elongated locking strips which are maintained in interlocked assembly. Extending from the locking strips are half staples, arranged in spaced relation along the length of the assembly locking strips. Prior to making the incision in the skin of the patient, the interlocked staple assembly is positioned with the assembled locking strips located immediately over the site of the incision. A stapler tool is then utilized to deform the staples of the staple assembly and thus cause the skin penetrating elements thereof to penetrate the skin and thereby establish a stapled, retaining relationship with the skin and the body tissues immediately below the skin. Adhesive strips will then be placed over the staples and in contact with the skin on each side of the locking strips to prevent the half staples from becoming unhooked from the skin when the locking strips are separated. After the interlocked staple assembly has been attached to the patient at the site of the incision, the surgeon will accomplish separation of the interlocking strips to thereby expose the skin of the patient immediately below the interlocked strips. The locking strips may be separated initially at the intermediate portion thereof while the end portions remain in interlocked assembly. The incision may then be made and the surgical procedure conducted. After completion of the surgical procedure, closure of the skin of the patient is accomplished simply by moving the locking strips together and applying sufficient mechanical pressure to cause the grooves and ridges thereof to become mechanically interlocked. Because of the stapled relationship of the strips to the skin of the patient, this movement causes the skin to be brought into intimately assembled relation to permit healing. Leakage of body fluid is permitted at the incision to prevent the development of trapped fluid which might cause infection.

If desired, the interlocking staple assembly may be provided with a mechanical opening and closing device which accomplishes opening and closing of the device in zipper-like fashion. Following completion of the surgical procedure, the incision may, therefore, be closed in a few seconds time as compared with many minutes of time ordinarily required for suturing.

BRIEF DESCRIPTION OF THE DRAWINGS

So that the manner in which the above-recited features of the present invention, which will become apparent, are attained and can be understood in detail, more particular description of the invention, briefly summarized above, may be had by reference to the embodiments thereof which are illustrated in the appended drawings, which drawings form a part of this specification.

It is to be noted, however, that the appended drawings illustrate only typical embodiments of the invention and are therefore not to be considered limiting of its scope, for the invention may admit to other equally effective embodiments.

IN THE DRAWINGS

Figure 1:
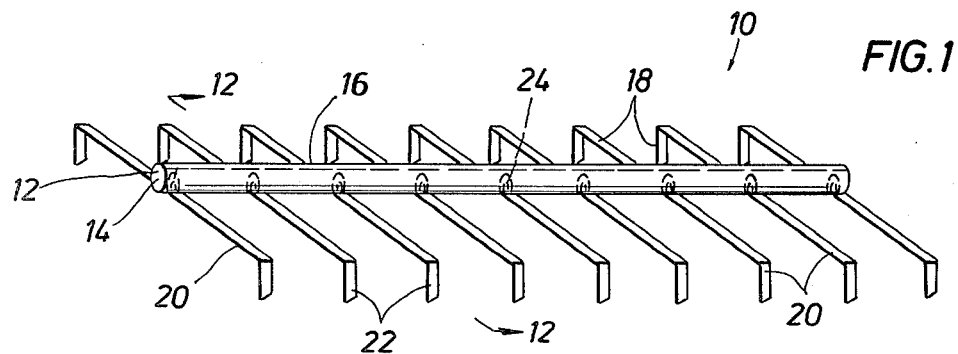

The present invention, both as to is organization and manner of operation, together with further objects and advantages thereof may best be understood by way of illustration and example of certain embodiments when taken in conjunction with the accompanying drawings in which:

FIG. 1 is an isometric representation of an interlocking and separatable surgical staple assembly constructed in accordance with the present invention.

Figure 2:
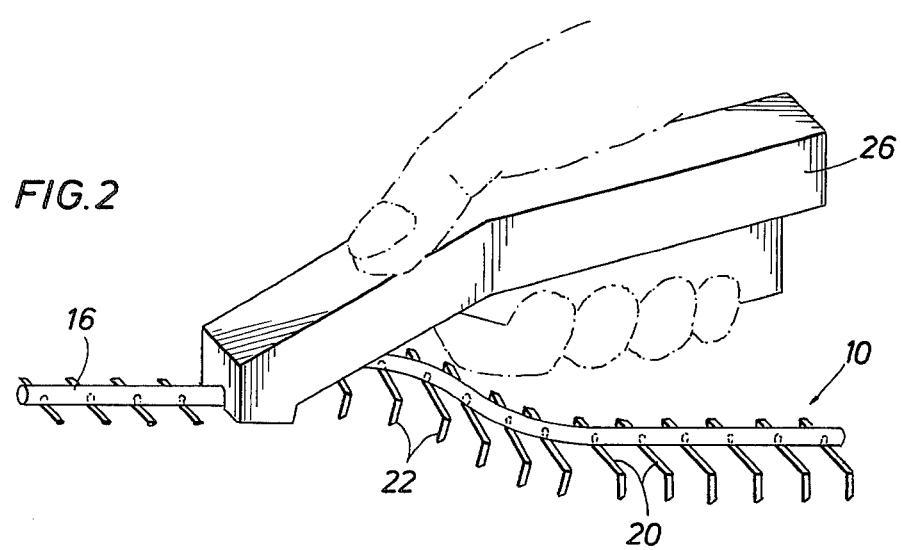

FIG. 2 is a pictorial representation illustrating presurgical attachment of the staple assembly of FIG. 1 to the skin of a patient prior to incision for surgery.

Figure 3:
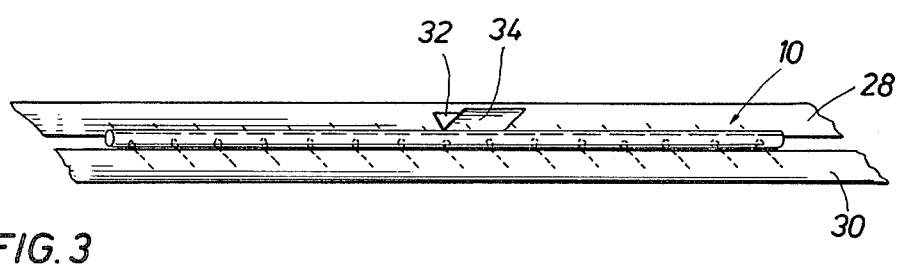

FIG. 3 is an isometric pictorial representation of the surgical staple assembly after illustration and with the staples being covered by means of surgical tape.

Figure 4:
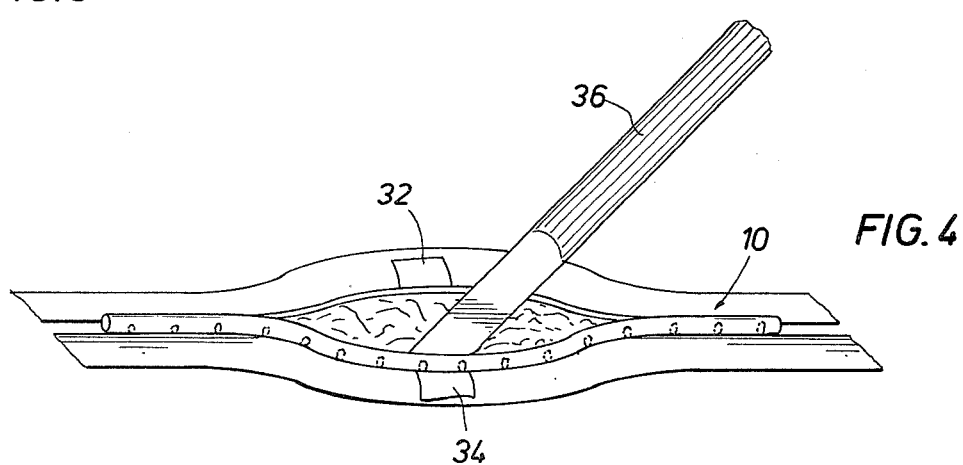

FIG. 4 is an isometric pictorial representation such as that shown in FIG. 3, but with the separatable interlocking strips of the staple assembly being separated intermediate the extremities thereof to permit conduct of the surgical procedure.

Figure 5:
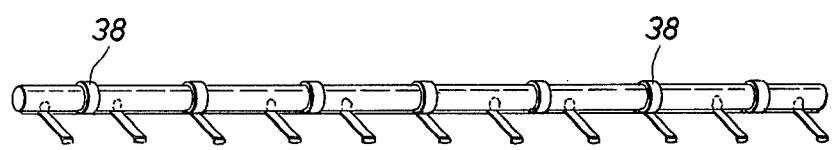

FIG. 5 is an isometric illustration of the surgical staple assembly illustrating a plurality of locking devices being utilized to positively secure a separable locking strips so as to prevent inadvertent separation thereof.

Figure 6:
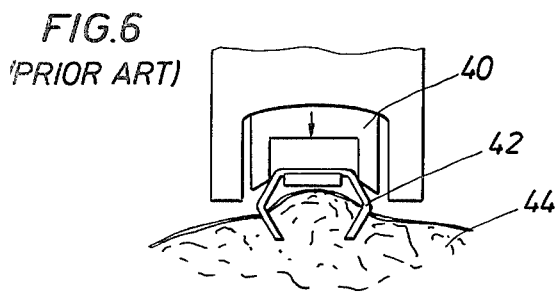

FIG. 6 is a transverse sectional view illustrating attachment of a staple to the skin of a patient by means of a stapling tool, which staple is representative of the prior art.

Figure 7:
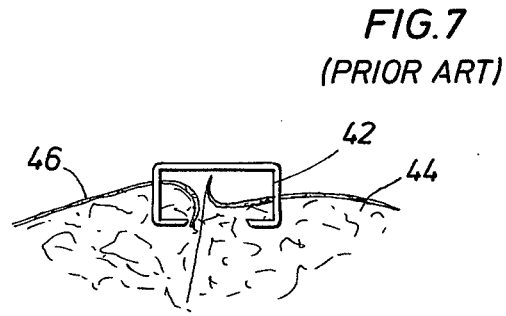

FIG. 7 is a sectional view similar to that of FIG. 6 and showing the prior art staple in its finished form and further illustrating undesirable overlapping of the skin of the patient.

Figure 9:
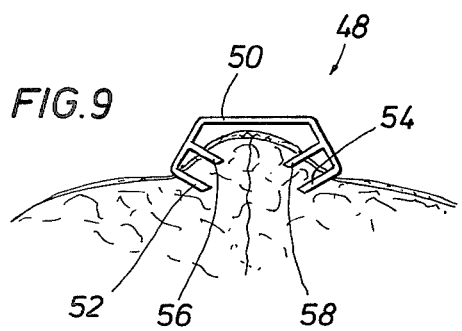
Figure 8:
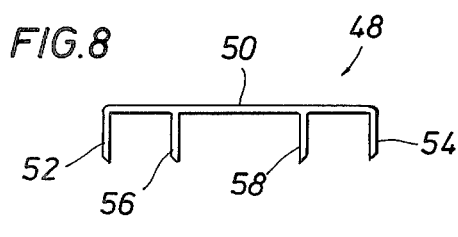

FIG. 8 is a pictorial representation of the staple of FIGS. 8 and 9, being shown in the undeformed condition thereof.

FIG. 9 is a sectional view similar to that of FIGS. 6 and 7 and illustrating an improved staple constructed in accordance with this invention and being assembled to the skin and body tissues of a patient.

Figure 10:
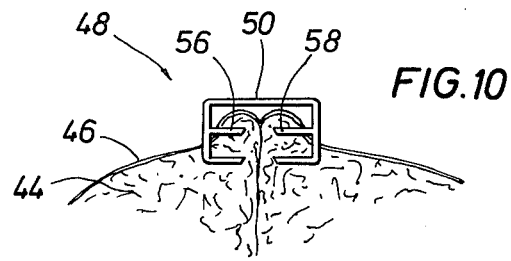

FIG. 10 is a sectional view similar to that of FIG. 8 and illustrating the staple in its finished form, securing the skin and body tissues of the patient in intimate, non-overlapping assembly.

Figure 11:
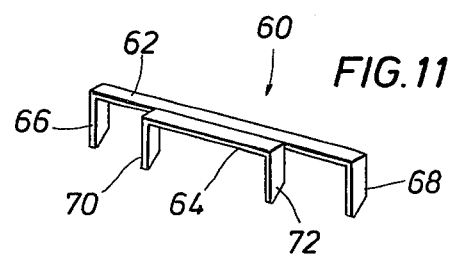

FIG. 11 is an isometric view of a staple construction representing an alternative embodiment of the present invention.

Figure 12:
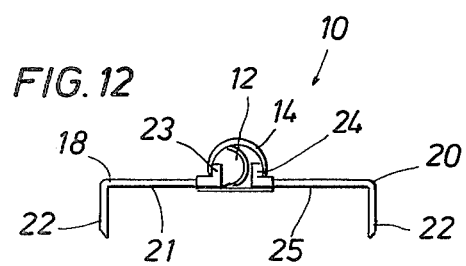

FIG. 12 is a sectional view taken along line 12—12 of FIG. 1.

Figure 13:
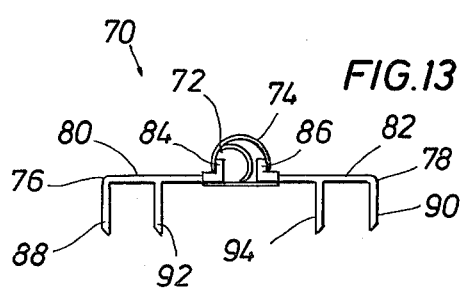

FIG. 13 is a sectional view similar to that of FIG. 1 and illustrating a staple construction incorporating plural skin penetrating projections positioned at each side thereof.

Figure 14:
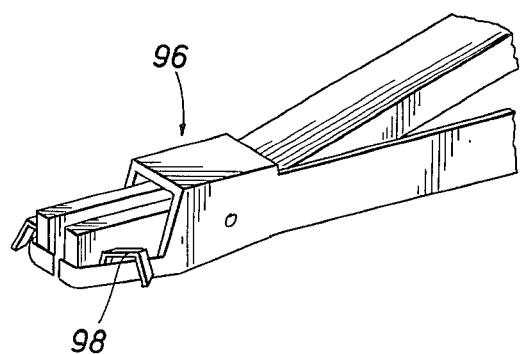

FIG. 14 is a pictorial representation of staple removal being accomplished by means of a staple removal tool.

Figure 15:
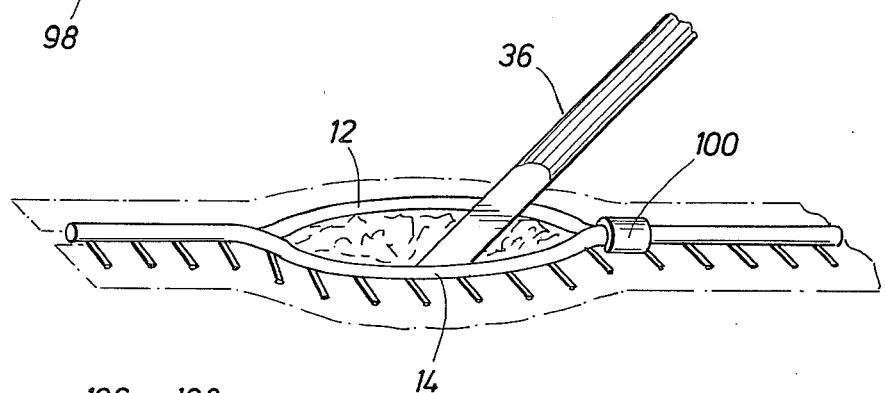

FIG. 15 is a pictorial representation of a surgical procedure being conducted through an opening defined by a separated portion of an interlocking staple assembly and further illustrating a mechanical closure for interlocking opposed locking strips in zipper-like fashion.

Figure 16:
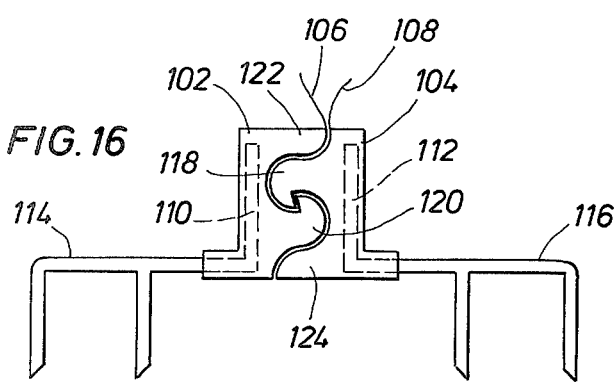

FIG. 16 is a sectional view of a staple construction representing a further modified embodiment of the present invention.

Figure 17:
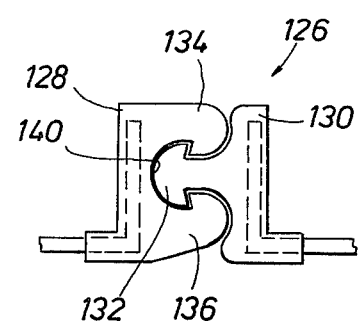

FIG. 17 is a fragmentary sectional view of a staple assembly representing another embodiment of this invention.

Figure 18:
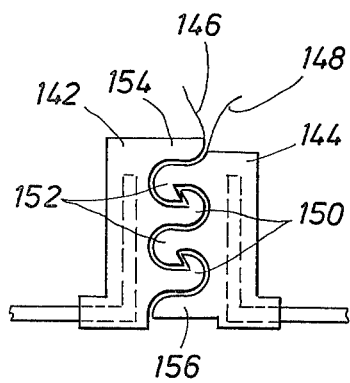

FIG. 18 is a fragmentary sectional view of the central portion of a staple assembly showing an interlocking mechanism and pull tabs for accomplishing separation of the locking strips thereof.

Figure 19:
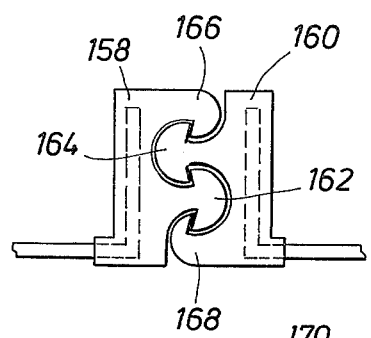
Figure 20:
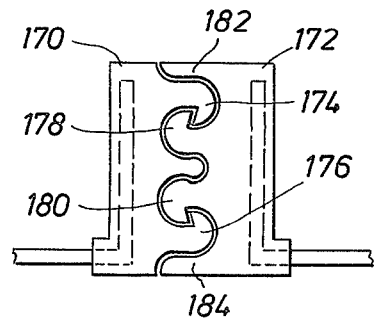

FIGS. 19 and 20 are also fragmentary sectional views representing modified locking strips for staple assemblies of the general form illustrated in FIG. 16.

Figure 21:
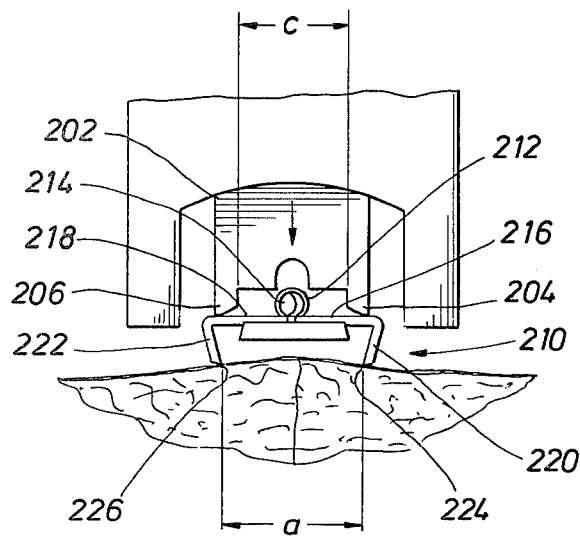

FIG. 21 is an end view of a staple assembly and staple gun representing a further embodiment of this invention and showing a preferred staple construction wherein the spacing of the skin penetrating elements is substantially the same as the spacing of the bending points of the staples.

Figure 22:
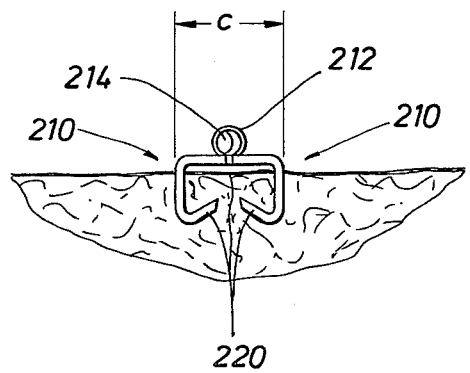

FIG. 22 is a sectional view showing the finished staple of FIG. 21 in retaining assembly with the skin tissue of a patient.

Figure 23:
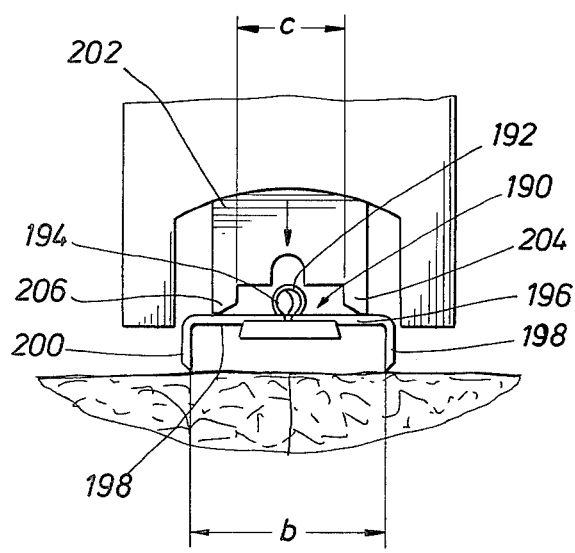

FIG. 23 is a view similar to that of FIG. 21 illustrating more conventional staple insertion into the skin tissue.

Figure 24:
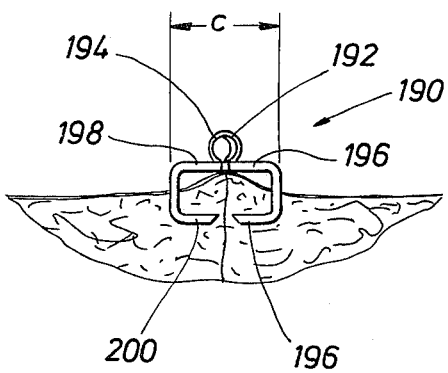

FIG. 24 is a sectional view similar to that of FIG. 22, illustrating the skin bulging effect that can be developed as the staple of FIG. 23 is inserted and bent to its final form by means of a staple gun.

DETAILED DESCRIPTION OF PREFERRED EMBODIMENTS

Referring now to the drawings and first to FIG. 1, a staple assembly is illustrated generally at 10 which comprises a pair of elongated locking strips 12 and 14 which are placed in interlocking assembly to form a locking strip 16. Each of the locking strips 12 and 14 are composed of flexible plastic material such as polyethylene or any other suitable material having the capability of being sterilized for use for surgical procedures. The locking strips are pliable, allowing them to be bent or formed according to the configuration of the incision to be made. This pliability also permits opening of the locking strips at the central portion thereof as will be more clearly evident below. Locking strips 12 and 14 incorporate interengaging ridges and grooves of any suitable design which permit the locking strips to be retained in interlocking assembly and also permit the locking strips to be separated for conduct of a surgical procedure and then brought back to interlocking relation following the surgical procedure. The staple assembly further incorporates a plurality of half staples such as shown at 18 and 20 which are of generally identical construction and which are secured to respective ones of the locking strips 12 and 14. As shown, a plurality of spaced half staples 18 are secured to the locking strip 12 while a plurality of spaced half staples are secured to the locking strip 14. Each of the half staples incorporates transversely projecting skin penetrating elements such as shown at 22 for the purpose of penetrating the skin and the body tissue of the patient immediately beneath the skin. The half staples are positioned in substantially evenly spaced relation along the length of the locking strips 12 and 14. The locking strips and thus the locking strip assembly 16 may be of any suitable length appropriate the accomplish the desired surgical procedure. If desired, the locking strip assembly may be provided in a suitable length for accomplishment of most surgical procedures, and may then be cut to the desired length in the operatory for the particular surgical procedure involved.

Each of the half staples is provided with a transversely oriented locking projection such as shown in broken line at 24 in FIG. 1, and in full line at 23 and 24 in FIG. 12. The locking projections are retained within the material of the locking strips, thus securing the staple halves in opposed, spaced relation.

As illustrated in FIG. 2, prior to making the incision for a surgical procedure, a stapling mechanism or stapling gun 26 is employed to deform the staples in the manner shown in FIGS. 6 and 7 to thus accomplish installation of the staple assembly 10 in assembly with the skin and subskin tissue of the patient. When assembled to the skin of the patient, as shown at the left hand portion of FIG. 2, each of the half staples is deformed and embedded in retaining relationship with the skin. In this position, the locking strip assembly 16 defined by the assembled locking strips 12 and 14 is positioned immediately over the intended site of the incision. After all of the staples have been attached to the skin of the patient, the staple assembly 10 will have the form generally illustrated in FIG. 3. The surgeon will then place adhesive tape 28 and 30 over the embedded half staples to prevent the half staples from becoming "unhooked" from the skin tissue when the locking strips are separated. When it is desired to accomplish incision, the surgeon or surgeon's assistant will grasp a pair of pull tabs 32 and 34 which extend from respective ones of the locking strips 12 and 14. Manual force is then applied to the pull tabs 32 and 34 resulting in separation of the interlocked locking strips with separation being initiated at the centermost portion of the elongated staple assembly 10. The locking strips are then separated or unlocked in such manner as to expose sufficient length to allow the incision to be accomplished by means of a scalpel 36. If the opening defined by the separated locking strips is of insufficient length, the surgeon may simply apply manual force to the unlocking tabs 32 and 34 or may grasp the opposed locking strips with forceps and simply pull them apart to gain additional length of opening of the incision. Although the locking strips may be completely separated, if desired, it is likely that the surgeon will ensure that the end portions thereof remain in interlocked assembly to facilitate ease of closing the incision after the surgical procedure has been completed. To close the staple assembly 10 and thus close the incision after completion of a surgical procedure, the surgeon will simply force the opened portion of the locking strips together thereby rendering the staple assembly to its completely locked condition as shown in FIG. 3.

Obviously, it is desirable to prevent inadvertent opening of the locking strips of the staple assembly and thus permit optimum healing at the incision. In accordance with the present invention, as shown in FIG. 5, a plurality of locking clips 38 may be applied in retaining manner about the assembled locking strips to thus ensure that the staple assembly remains closed.

FIGS. 6 and 7 represent the prior art method of assembling skin tissue at surgical incisions. As shown in FIG. 6, a staple gun 40 is employed to achieve application of a staple 42 in the skin tissue 44. The staple 42 is shown partially embedded in the skin tissue and partially deformed from its original configuration, toward the installed configuration thereof as shown in FIG. 7. FIG. 7 is representative of the completed configuration of the staple 42 and identifies a problem that is common to stapling type closure of incisions. As the staple 42 is deformed from its original condition, to the partially deformed configuration of FIG. 6 and then to the finished configuration of FIG. 7, the sub-skin body tissues 44 will be forced together. In many cases the skin tissue 46 is forced into overlapping relation as shown in FIG. 7 as the staple is deformed to its final configuration. Obviously, overlapping of the skin tissues is undesirable since it results in improper joining of the skin tissues at the incision and also provides opportunity for infection by virtue of the overlapped skin tissues. It is desirable therefore to provide a staple configuration having the capability of forcing the sub-skin and skin tissues in proper assembly upon application of the staple to thus ensure that the skin tissues are not overlapped. In accordance with the present invention, an improved staple is provided as shown generally at 48 in FIGS. 8-10. The staple 48 incorporates an elongated staple bar 50 having outer skin penetrating elements 52 and 54 extending in substantially normal relation from the end portions thereof. The staple construction 48 also incorporates spaced intermediate skin penetrating elements 56 and 58 which are also disposed in substantially normal relation with the elongated bar 50 and are essentially parallel with the skin penetrating elements 52 and 54. As shown in FIG. 9 the staple construction 48 is illustrated in its partly deformed configuration as it is deformed by a staple gun similar to that of FIG. 6. In FIG. 10 the staple construction 48 is shown in its finished configuration after having been fully deformed by the staple gun. As shown in FIG. 10, the opposed portions of the skin tissue 44 are drawn together tightly and the intermediate staple portions 56 and 58 will, in this condition, be located relatively close to the skin tissue 46. The intermediate skin penetrating elements will thus effectively position the skin tissue at the incision to thus prevent it from being positioned in overlapping relation. By thus positioning the skin tissues and the sub-skin in the manner illustrated in FIG. 10 the staple construction 48 will promote efficient healing at the incision.

As shown in FIG. 11, a modified embodiment of the invention is illustrated generally at 60. The staple construction 60 incorporates a pair of elongated staple bars 62 and 64 which are joined together or which may be formed integrally. The elongated bar 62 is of greater length than bar 64 and incorporates a pair of skin penetrating elements 66 and 68 which project transversely from the end portions thereof. Skin penetrating elements 70 and 72 project transversely from the end portions of the shorter elongated bar 64 in the manner illustrated. The staple 60 is shown in its undeformed condition prior to installation. Upon being completely installed, it will be deformed essentially as shown in FIGS. 9 and 10. Here again, the intermediate skin penetrating elements 70 and 72 will be located immediately beneath the skin tissue of the patient and will thereby ensure optimum positioning of the skin tissues in joining relation and will prevent any condition of skin overlap as shown in FIG. 7.

Referring now to FIG. 12, an end view of the staple assembly of FIG. 1 is illustrated generally at 10. The staple assembly 10 is shown in its undeformed condition with the skin penetrating elements 22 of the half staples 18 and 20 extending transversely from the staple bars 21 and 25. When the staple 10 is installed in the body tissues of the patient, the bar portions 21 and 25 thereof will be bent to such extent that the skin penetrating elements will be positioned in spaced, opposed relation in the manner illustrated in FIG. 7.

As shown in FIG. 26, a staple assembly is illustrated generally at 70 which incorporates elongated locking strips 72 and 74 which are composed of any suitable flexible plastic material. A plurality of staples are positioned along the length of the flexible locking strips 72 and 74 in the manner illustrated in FIG. 1. Each of the staples comprises a pair of half-staples such as shown at 76 and 78, each having elongated bar portions 80 and 82 respectively. The bar portions are formed at the inner extremities thereof to define upwardly projecting locking portions 84 and 86 which are retained by the plastic material of the elongated locking strips 72 and 74. Preferably, the locking strips 72 and 74 are molded about the locking projections 84 and 86. At the outer extremities of each of the staple bars 80 and 82, tissue penetrating elements 88 and 90 extend in transverse relation to the bar portions. Inner tissue penetrating elements 92 and 94 also extend in transverse relation from the bar portions 80 and 82 of the half-staples and are positioned in spaced, parallel relation with the respective end tissue penetrating elements 88 and 90. The half-staples 76 and 78 are deformed during installation by bending the elongated bar portions 80 and 82 at points between the locking projections 84 and 86 and the inner tissue penetrating elements 92 and 94. Upon bending of the staple in this manner it will assume the general configuration illustrated in FIG. 10 with opposed pairs of tissue penetrating elements positioned in spaced, opposed relation. The inner tissue penetrating elements 92 and 94 will be positioned in close proximity to the skin while the outer skin penetrating elements 88 and 90 will be positioned more deeply within the body tissue essentially as shown in FIG. 10.

In FIG. 14 a staple removal tool is shown generally at 96 which is adapted for removal of staples in the manner shown at 98. The staple removal tool 96 will take the same general form regardless whether the staples are of the double penetrating type as shown in FIG. 13 or the single penetrating type as shown in FIG. 12. The staple 98 shown in FIG. 14 is of the single penetrating type essentially as shown in FIG. 12.

As mentioned above, after the surgical procedure has been completed, it will be desirable to close the incision and such is accomplished simply by forcing the separated portions of the locking strips to the assembled relation thereof. As shown in FIG. 5, the locking strips are shown with the intermediate portions thereof separated with a scalpel 36 being utilized to form the incision. After completion of the surgical procedure the scalpel of course will not be present. The opposed locking strips 12 and 14 may be bought into interlocked assembly by means of a closure element 100 which is slidable along the length of the locking strip portions of the staple assembly. The closure member 100 functions in the manner of a zipper and which is merely moved along the length of the staple assembly. Its structural relationship with the staple assembly is such that it is received closely about the locking strips and conforms approximately to the locked configuration thereof. Thus, as the closure member 100 is moved linearly along the length of the opened staple assembly of FIG. 15, the locking strips are brought into assembled, interlocking relation essentially as shown in FIG. 3. After the locking strips have been brought to the interlocking relationship thereof essentially as shown in FIG. 3, locking clips may be applied as shown at 38 in FIG. 5 to ensure that the locking strips remain in positive locked assembly during healing of the skin tissue. After healing, the staples may be removed by means of a staple remover such as shown at 96 in FIG. 14.

Referring now to FIGS. 16–20, the locking strips may take other suitable forms without departing from the spirit and scope of the present invention. As shown in FIG. 16, locking strips are shown as 102 and 104 which have opening tabs 106 and 108 affixed thereto essentially as shown at 32 and 34 in FIG. 3. Each of the locking strips 102 and 104 are molded about locking projection portions 110 and 112 of staple halves 114 and 116. The locking strips are formed with interlocking hooked projections 118 and 120 which are received within respective locking grooves and establish interlocking relation with one another. These hooked locking projection portions 118 and 120 cooperate to lock the strips securely closed. Projecting strip portions 122 and 124 cooperate with the adjacent hooked shaped strips to define grooves and thus enhance the locking capability of the locking strips. The locking strips permit fluid leakage at the incision to thus prevent any trapped build up of body fluid which could result in the development of infection.

In FIG. 17, a modified staple assembly is shown generally at 126 having locking strips 128 and 130. Locking strip 130 defines a double hooked projection 132 which is received between hooked projections 134 and 136 of the locking strip 128. The hooked projections 134 and 136 are spaced and define a locking groove 140 between them for receiving the double hooked portion 132 of locking strip 130. It should be borne in mind that the hooked projecting portions such as shown at 132, 134 and 136 are in the form of elongated strips that establish interlocking relation upon being forced to the interlocking relation thereof as shown in the figures.

As shown in FIG. 18 opposed locking strips are shown at 142 and 144 which are provided with opening tabs 146 and 148. Each of these locking strips define a pair of spaced locking projections such as shown at 150 and 152 which establish locking grooves between them within which the opposed locking projections are received. Portions 154 and 156 are also provided on the locking strips to enhance the locking capability of the strips when they are brought into interlocking assembly.

As shown in FIG. 19, locking strips 158 and 160 are shown each of which defines double hooked projecting portions 162 and 164 respectively which are received within locking grooves defined by upper and lower hooked portions 166 and 168 and by the interlocking relation between the double hooked portions. The upper and lower hooked portions 166 and 168 also function to assist in the locking retention of the locking strips.

As shown in FIG. 20 locking strips 170 and 172 are shown. Locking strip 170 defines two spaced oppositely directed hooked portions 174 and 176 between which are received the oppositely directed spaced hook projections 178 and 180 of the locking strip 172. Upper and lower sealing strip portions 182 and 184 also enhance the locking capability of the assembled locking strips.

Especially where staple assemblies are employed having single skin penetrating elements at each side thereof it may be desirable to provide a staple configuration which, by its construction, eliminates the development of a skin bulge as the staple is inserted and then bent to its final form by means of a staple gun. As shown in FIG. 23, a staple assembly is illustrated generally at 190 which incorporates separatable locking strips 1902 and 194 and which incorporates half staples each having staple bars 196 and 198 respectively from which extend skin penetrating elements 198 and 200. In the case of the staple construction of FIG. 23 the skin penetrating elements 198 and 200 extend in substantially normal relation with the respective bar portions 196 and 198 of the staple assembly. In this position the skin penetrating elements will readily penetrate the skin tissue of the patient simply by applying downward pressure by means of the staple gun 202. It should be noted that the staple bending elements 204 and 206 of the staple gun define a spacing C which is less than the spacing B of the skin penetrating elements 198 and 200. As the staple halves are bent by the staple bending elements 204 and 206 after penetration of the skin penetrating elements the staple will likely have a final form as indicated in FIG. 24. Thus, the staple bars 196 and 198 are bent at the points of contact by the staple bending elements 204 and 206 thereby causing the bending points to define the spacing C as shown in FIG. 24. As the staple bends from the position shown in FIG. 23 toward the position shown in FIG. 24 the skin tissue will be gathered thereby resulting in a bulge as shown in FIG. 24. This is caused by the fact that the skin penetrating elements 198 and 200 are spaced at a distance greater than the spacing of the bending points shown at C in FIGS. 23 and 24. After the locking strips have been separated and the incision has been made, it may be difficult to retain the staple halves in assembly with the skin tissue. The staple halve may simply unhook from the skin allowing the skin penetrating elements to release the skin. Further, upon closure of the incision by moving the locking strips into locked assembly, it is possible for the bulged skin tissue to become overlapped. Should this occur, obviously healing at the skin tissue could be retarded and undesirably shaped scar tissue could result therefrom.

As shown in FIGS. 21 and 22, the present invention may take another suitable form as illustrated generally at 210. In this case, locking strips are provided as shown at 212 and 214 to which are secured staple halves each defining staple bars 216 and 218. Skin penetrating elements 220 and 222 extend respectively from the staple bars 216 and 218 and are positioned in angulated relation with respect to the staple bars such that the points 224 and 226 thereof engage the skin tissue of the patient at a spacing A which is essentially identical to the spacing C established by the bending contact points of the bending elements 204 and 206 of the staple gun with the bar portions 216 and 218 of the staple assembly. Thus, as the staple 210 is bent from the configuration shown in FIG. 21 to the finished form shown in FIG. 2 it will not gather the skin tissue because the spacing of staple penetration is relatively the same as the spacing of the staple bending points. The finished staple form will then have the configuration shown in FIG. 22 with the skin penetrating elements 220 and 222 being positioned in upwardly inclined relation toward the skin tissue. After the locking strips 212 and 214 of the staple assembly have been separated so that the incision can be made, the upwardly inclined skin penetrating elements will tend to be efficiently retained in engaged assembly with the skin tissue. Thus, the staple halves will readily remain in engaged relation with the skin tissue and it will not be necessary to employ adhesive tape such as shown in FIGS. 3 and 4 for staple retention. Moreover, since the skin tissue is not pulled together and bulged as the staple is bent to its final form, movement of the locking strips 212 and 214 to the locked relation thereof as shown in FIG. 22 will simply position the skin tissue in optimum, abutting relation.

Although FIGS. 16-24 illustrate various possible configurations of the locking strips, these figures are by no means restrictive of the possible configurations thereof. The locking strips may take any one of a number of suitable forms within the spirit and scope of the present invention.

In view of the foregoing it is therefore seen that my invention is one well adapted to attain all of objects and advantages hereinabove set forth together with other advantages which will become obvious and inherent from a description of the apparatus itself. It will be understood that certain combinations and subcombinations are of utility and may be employed without reference to other features and subcombinations. This is contemplated by and is within the scope of the present invention.

What is claimed is:

1. A skin opening and closure device for surgical procedures, comprising:
    (a) first and second elongated locking strips each having elongated mating locking ridge means formed thereon, said locking ridge means of said locking strips releasably securing said locking strips in assembly along the lengths thereof and being locatable along the length of an intended surgical incision;
    (b) a plurality of staple elements being secured in spaced relation along the length of each of said locking strips for securing said locking strips to the skin of a patient undergoing surgery; and
    (c) with said staple elements secured to the skin of the patient, said locking strips being separatable to expose the skin of the patient along the line of intended incision and upon completion of the surgical procedure being forcible into interlocking assembly to close the incision.

2. A skin opening and closure device as recited in claim 1, including:

positive lock means being securable to said first and second locking strips along the length thereof when in interlocked assembly to prevent inadvertent separation of said locking strips.

3. A skin opening and closure device as recited in claim 1, wherein:
said locking strips are each formed of yieldable plastic material and, when in interlocked relation, are capable of being selectively separated along a portion of the length thereof to expose the length of the patient's skin as is desirable for accomplishing the surgical procedure.

4. A skin opening and closure device as recited in claim 1, wherein said staple elements comprise:
(a) first half staple means being secured to one of said locking strips; and
(b) second half staple means being secured to the other of said locking strips.

5. A skin opening and closure device as recited in claim 4, wherein:
each of said first and second half staple means defines at least one skin penetrating element and cooperates with an opposite half staple means to form a mechanically deformable staple assembly, said staple assembly being deformable during installation to shift said skin penetrating elements into spaced, opposed relation, thus permitting said staple assembly to close the incision.

6. A skin opening and closure device as recited in claim 4, wherein:
each of said first and second half staple means defines a pair of spaced skin penetrating elements and cooperate with an opposite half staple means of the opposite locking strip to define a mechanically deformable staple assembly, said staple assembly being deformable during installation to shift said pairs of skin penetrating elements from a generally parallel relation to a spaced, opposed relation, thus permitting said staple assembly to close the patient's skin and maintain the skin in non-overlapping relation at the incision, said locking strips being separatable along a desired portion of the length thereof following insertion of said staple assemblies to permit incision and surgery between said half staple means and being lockable to close the incision at the completion of the surgical procedure.

7. A skin opening and closure device as recited in claim 4, including:
elongated positive lock means being securable in locking assembly with said locking strips in the interlocked relation thereof and preventing inadvertent separation of said locking strips.

8. A skin opening and closure device as recited in claim 1, including:
opening tab means being secured to each of said first and second locking strips and being manually manipulated to accomplish forcible separation of said locking strips from the interlocked relation thereof.

9. A skin opening and closure device as recited in claim 1, wherein said staple means comprises:
(a) a pair of elongated staple bars;
(b) skin penetrating projection means extending transversely from each of said staple bars; and
(c) locking projection means extending from each of said staple bars and being secured to respective ones of said locking strips.

10. A skin opening and closure device as recited in claim 9, wherein:
said locking projection means is embedded within the material defining said locking strips.

11. A skin opening and closure device as recited in claim 1, wherein:
(a) said first and second locking strips are capable of being moved into interlocking assembly and separated by zipper-like activity; and
(b) a slide element is in movable assembly with said locking strips and is manually movable in linear manner along the length of said locking strips to achieve selective interlocking and separation of said locking strips.

12. A skin opening and closure device as recited in claim 1, wherein:
said first and second locking strips are capable of being forced into interlocking assembly and separated along the length thereof by application of manual force thereto.

13. A method of opening and closing skin tissue during a surgical procedure, comprising:
(a) securing staple means to the skin tissue of a patient along the length of the surgical incision, the center of said staple mean being located above the site of the incision, said staple means comprising locking strips having half staples assembled along the length thereof and extending therefrom in spaced relation along the length thereof;
(b) separating said locking strips along at least a portion of the length thereof to expose the line of the intended incision;
(c) making the surgical incision along the selected line; and
(d) closing the surgical incision following completion of the surgical procedure by bringing said locking strips to closed and locked assembly along the length thereof thus closing the skin tissue at the incision.

14. The method recited in claim 13, wherein:
said separating of said locking strips is accomplished by application of opposing force to the intermediate portions of the assembled locking strips, thus separating them at the intermediate portion only, the extremities thereof remaining in locked assembly.

15. The method recited in claim 13, wherein:
said locking strips are forced together by zipper closure means manually moved along the length of said locking strips and accomplishing closing and locking of said locking strips along the length thereof.

16. A skin opening and closure device for surgical procedures, comprising:
(a) first and second elongated mating locking strips each having elongated locking ridge means formed along the length thereof, said locking ridges of said locking strips releasably securing said locking strips in assembly along the lengths thereof and being locatable along the length of an intended surgical incision;
(b) a plurality of half staple elements being secured to each of said locking strips in spaced relation along the length thereof and defining elongated staple bar means positioned in generally coextensive relation, said staple bar means each defining bending points positioned in spaced relation; and (c) skin penetrating elements extending from each of said staple bar means and defining skin penetrating points, said skin penetrating elements being positioned in converging relation with one another such that the spacing of said skin penetrating points is substantially the same as the spacing of said bending points.

17. A skin opening and closure device as recited in claim 16, wherein:
   (a) said skin penetrating elements are positioned at the extremities of said staple bar means and are formed integrally therewith; and
   (b) said skin penetrating elements are oriented in acute angular relation with said staple bar means.

18. A skin opening and closure device as recited in claim 16, wherein:
   said bending points of said staple bar means are determined by the points of bending contact thereof with bending elements of a staple gun.

19. A skin opening and closure deviceas recited in claim 16, wherein:
   said skin penetrating points are located in spaced relation with said staple bar means and are positioned intermediate the extremities of said staple bar means.

* * * * *